US008831322B2

(12) United States Patent  
Abboud

(10) Patent No.: US 8,831,322 B2
(45) Date of Patent: Sep. 9, 2014

(54) METHOD OF GENERATING A THREE-DIMENSIONAL DIGITAL RADIOLOGICAL VOLUME TOPOGRAPHY RECORDING OF A PATIENT'S BODY PART

(76) Inventor: Marcus Abboud, Setauket, NY (US)

(*) Notice: Subject to any disclaimer, the term of this patent is extended or adjusted under 35 U.S.C. 154(b) by 87 days.

(21) Appl. No.: 13/432,355

(22) Filed: Mar. 28, 2012

(65) Prior Publication Data
US 2012/0263363 A1 Oct. 18, 2012

(30) Foreign Application Priority Data
Apr. 12, 2011 (EP) .................................... 11162043

(51) Int. Cl.
G06K 9/00 (2006.01)
A61C 19/04 (2006.01)
G06T 11/00 (2006.01)
A61B 6/14 (2006.01)
G06T 3/40 (2006.01)
A61B 6/00 (2006.01)
A61B 6/12 (2006.01)

(52) U.S. Cl.
CPC ............... *A61B 6/466* (2013.01); *G06T 11/008* (2013.01); *A61B 6/14* (2013.01); *G06T 3/40* (2013.01); *A61B 6/583* (2013.01); *A61B 6/12* (2013.01)
USPC ................. 382/131; 382/128; 433/68; 433/69

(58) Field of Classification Search
USPC ................................................. 382/131, 132
See application file for complete search history.

(56) References Cited

U.S. PATENT DOCUMENTS

| 6,259,943 | B1* | 7/2001 | Cosman et al. | 600/429 |
| 6,351,573 | B1* | 2/2002 | Schneider | 382/294 |
| 6,394,802 | B1* | 5/2002 | Hahn | 433/37 |
| 6,640,127 | B1* | 10/2003 | Kosaka et al. | 600/426 |
| 7,182,737 | B2* | 2/2007 | Kim et al. | 600/590 |

(Continued)

FOREIGN PATENT DOCUMENTS

GB 2 449 113 A 11/2008
WO WO 99/44503 A1 9/1999

(Continued)

OTHER PUBLICATIONS

Cucchiara et al. "An image analysis approach for automatically re-orienteering CT images for dental implants", Computerized Medical Imaging and Graphics 29 (2004) 180-201, 2004.*

Primary Examiner — Anand Bhatnagar
Assistant Examiner — Soo Park
(74) Attorney, Agent, or Firm — Norman B. Thot

(57) ABSTRACT

A method for generating a radiologic three-dimensional digital volume tomography image of a patient's body part includes fixing a marker support to the patient's body part. The marker support is provided with a non-radioopaque support body in which a plurality of radioopaque marker elements are affixed. A nominal size S and/or a nominal distance D of the radioopaque marker elements to each other is known. The body part is image recorded with a digital volume tomography device so as to generate a three-dimensional raw image of the patient's body part. A size S' and/or a distance D' of the radioopaque marker elements in the three-dimensional raw image is measured. An aberration value is generated by comparing the size S' and/or the distance D' with the respective nominal size S and/or the nominal distance D of the radioopaque marker elements. The three-dimensional raw image is corrected with the aberration value.

14 Claims, 2 Drawing Sheets

(56) References Cited

U.S. PATENT DOCUMENTS

| | | | |
|---|---|---|---|
| 7,702,380 B1 | 4/2010 | Dean | |
| 7,899,512 B2 * | 3/2011 | Labadie et al. | 600/407 |
| 8,172,573 B2 * | 5/2012 | Sonenfeld et al. | 433/173 |
| 8,215,957 B2 * | 7/2012 | Shelton | 433/75 |
| 8,363,919 B2 * | 1/2013 | Sebok | 382/131 |
| 8,602,773 B2 * | 12/2013 | Karlsson et al. | 433/46 |
| 2001/0034482 A1 | 10/2001 | Webber et al. | |
| 2003/0086535 A1 | 5/2003 | Teppaz et al. | |
| 2004/0121282 A1 * | 6/2004 | Sildve et al. | 433/37 |
| 2006/0281991 A1 * | 12/2006 | Fitzpatrick et al. | 600/426 |
| 2007/0122020 A1 | 5/2007 | Claus et al. | |
| 2007/0141525 A1 * | 6/2007 | Cinader, Jr. | 433/23 |
| 2007/0172123 A1 * | 7/2007 | Komatsubara et al. | 382/175 |
| 2008/0286715 A1 * | 11/2008 | Choi | 433/37 |
| 2009/0018437 A1 | 1/2009 | Cooke | |
| 2009/0042167 A1 * | 2/2009 | Van Der Zel | 433/215 |
| 2009/0086887 A1 | 4/2009 | Kito et al. | |
| 2009/0179986 A1 * | 7/2009 | Klett | 348/77 |
| 2009/0209852 A1 * | 8/2009 | Mate et al. | 600/431 |
| 2009/0285366 A1 * | 11/2009 | Essenreiter et al. | 378/207 |
| 2010/0014750 A1 * | 1/2010 | Seko et al. | 382/154 |
| 2010/0086185 A1 * | 4/2010 | Weiss | 382/131 |
| 2010/0268071 A1 * | 10/2010 | Kim | 600/426 |
| 2010/0278311 A1 | 11/2010 | Hammerstrom et al. | |
| 2011/0230755 A1 * | 9/2011 | MacFarlane et al. | 600/414 |
| 2012/0028211 A1 * | 2/2012 | Palti | 433/71 |

FOREIGN PATENT DOCUMENTS

| | | |
|---|---|---|
| WO | WO 01/33511 A2 | 5/2001 |
| WO | WO 02/32307 A1 | 4/2002 |
| WO | WO 2004/100767 A2 | 11/2004 |
| WO | WO 2006/094156 A2 | 9/2006 |
| WO | WO 2010085981 A1 * | 8/2010 |

\* cited by examiner

METHOD OF GENERATING A THREE-DIMENSIONAL DIGITAL RADIOLOGICAL VOLUME TOPOGRAPHY RECORDING OF A PATIENT'S BODY PART

CROSS REFERENCE TO PRIOR APPLICATIONS

Priority is claimed to European Patent Application No. EP 11162043.1, filed Apr. 12, 2011. The entire disclosure of said application is incorporated by reference herein.

FIELD

The present invention provides a method for generating a radiologic three-dimensional digital volume tomography image of a patient's body part, in particular, of a patient's head, for example, of a patient's jaw.

BACKGROUND

Digital volume tomography is often used as an imaging radiologic tomography method in dental and otorhinolaryngologic applications. In digital volume tomography, a cone-shaped X-ray beam is directed onto a two-dimensional detector arranged at a constant distance opposite the same. The arrangement, consisting of the X-ray source and the detector, is moved around the patient's head during a scan, each scan taking 10-30 seconds.

Compared to other three-dimensional imaging radiologic methods, digital volume tomography has the advantage of a relatively low radiation exposure of a patient. However, the quality of the three-dimensional images of a patient's head thus obtained and calculated varies considerably and is hard to assess. The reasons for the varying image quality are, on the one hand, principle-related and of physical nature and, on the other hand, are due to the long scan time which makes it impossible to exclude undesirable self-motions of a patient's head, the X-ray source and the detector during a scan. Self-motions have a considerable negative effect on the image quality. In practice, the size ratios and proportions in the three-dimensional image are often represented with an error margin of up to several millimeters. Although this is not always problematic in diagnostics, digital volume tomography is, however, also used in dentistry to plan dental implants in a patient's jaw. This requires a high geometric accuracy so as to provide a high quality of the implant treatment.

SUMMARY

An aspect of the present invention is to provide a method for generating a radiologic three-dimensional volume tomography image, in particular, a digital volume tomography image, of a patient's body part with the possibility of quality control and/or enhanced accuracy.

In an embodiment, the present invention provides a method for generating a radiologic three-dimensional digital volume tomography image of a patient's body part which includes fixing a marker support to the patient's body part. The marker support is provided with a non-radioopaque support body in which a plurality of radioopaque marker elements are affixed. At least one of a nominal size S and a nominal distance D of the radioopaque marker elements to each other is known. The body part is image recorded with a digital volume tomography device so as to generate a three-dimensional raw image of the patient's body part. At least one of a size S' and a distance D' of the radioopaque marker elements in the three-dimensional raw image is measured. An aberration value is generated by comparing at least one of the size S' and the distance D' of the radioopaque marker elements in the three-dimensional raw image with the respective at least one of the nominal size S and the nominal distance D of the radiopaque marker elements. The three-dimensional raw image is corrected with the aberration value.

BRIEF DESCRIPTION OF THE DRAWINGS

The present invention is described in greater detail below on the basis of embodiments and of the drawings in which.

DETAILED DESCRIPTION

Figure 1:
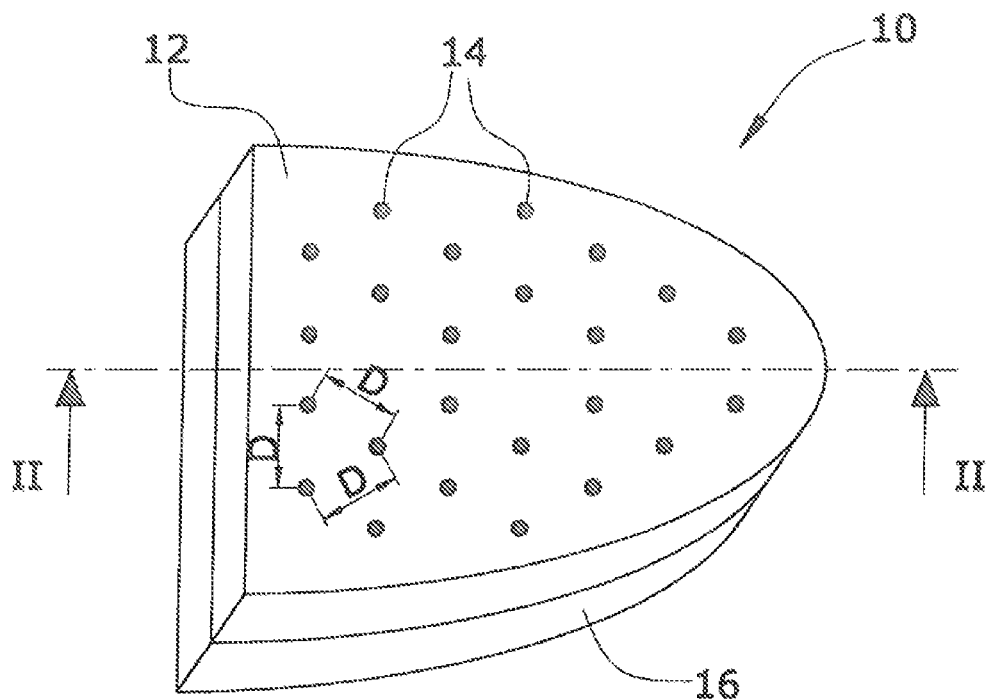
FIG. 1 shows a perspective view of an oral marker support.

The present invention provides that, prior to generating the image, a marker support is fixed on the patient's body part, for example, in the patient's mouth. The marker support may, for example, include an individually-shaped element formed from the patient's jaw with which the marker support can be positioned on the patient's jaw in a form-fitting and immovable manner. The fixation can be provided by the patient biting thereon.

The marker support comprises a non-radioopaque support body that absorbs virtually no X-ray radiation and is thus substantially invisible to an X-ray apparatus. A plurality of radioopaque marker elements are fixed at or in the support body, whose nominal size S and/or mutual nominal distance D is known.

The digital volume tomography apparatus is first used to make a scan of the relevant body part, such as a patient's jaw, to generate a three-dimensional raw image of the body part, as is known from prior art. Measurements are thereafter made in the raw image for some or all of the marker elements with respect to the size S' and/or the mutual distances D' of the marker elements.

The measured values of the marker element size S' or the marker element distances D' are compared with the respective nominal values S, D, and a calibration value QS, QD is generated therefrom. This calibration value QS, QD may, for example, be the respective quotient from the respective nominal value S, D and the measured values S', D'.

The raw image is thereafter corrected on the basis of the calibration values QS, QD obtained. The raw image may be normalized, for example, by stretching or compressing the image by the value of the quotient from the nominal value and the measured value. The corrected three-dimensional image of the body part or a patient's jaw, thus obtained, is significantly more accurate than the raw image, in particular with respect to the proportions and distances. In this manner, an exact three-dimensional image of a patient's jaw is provided, in particular, for the planning of dental implants, which image forms the basis for the subsequent exact planning and realization of the implantological dental treatment.

In an embodiment of the present invention, the correction can, for example, be a size correction of the raw image based on the raw image distances D' in relation to the mutual nominal distances D of the marker elements. From the quotient of the raw image distances D' and the nominal distances D of the marker elements, a correction value can be generated directly by which the raw image should be corrected. As an alternative, or in addition thereto, a quality indicator can be outputted whose value results from the aberration of raw image size S' from the nominal size S of the marker elements. It is thus again possible to use a quotient as the basis for the quality indicator. The size quality indicator provides information about the quality degree of the raw image at the position of the respective marker element. In the event of shakes and blurs in the raw image, the marker element is, for example, reproduced much larger in the raw image than it actually is. It is true that the quality indicator does not allow for an immediate correction of the raw image, however, it provides the user of the raw image with information about how much the user can rely on the raw image.

In an embodiment of the present invention, at least 10 marker elements can, for example, be provided, with each marker element being arranged at a constant nominal distance of at most 3.0 cm from its neighbor marker elements. A grid of marker elements is thus set up whose mesh width is constant over the entire grid and has a maximum of 3.0 cm. This offers the possibility to perform a local size correction at several locations in the raw image based on the raw image distances D' in relation to the nominal distances D. This gives consideration to the fact that the blurs in the raw image may actually be different locally.

The marker elements may be distributed either two-dimensionally or spatially and may be arranged on lines that are at right angles to each other. Three neighboring marker elements can, for example, form an equilateral triangle. With such an arrangement, a grid with a sufficient density of marker elements can be set up in a relevant space using relatively few marker elements that may themselves be a source of artifacts because of their radioopacity.

In an embodiment of the present invention, the marker elements can, for example, be arranged on at least two transversal planes, i.e., on two horizontal planes. It is thereby provided that the size correction of the raw image can be performed for all three spatial axes based on the mutual distances D, D' of the marker elements.

In an embodiment of the present invention, the radioopacity of the marker elements can, for example, differ. Since, due to their radioopacity to X-ray radiation, the marker elements also have reflexive properties that depend on the degree of radioopacity, it is possible, for example, by reducing the radioopacity of the marker elements, in particularly, sensitive regions, to reduce or avoid artifacts in these regions.

In an embodiment of the present invention, a calibration of the raw image brightness can be performed based on the known different radioopacity values of the marker elements. For example, the radioopacity values of the marker elements can comprise three to six different values so that approximately the entire radioopacity spectrum of the body part to be scanned is covered. An objective measure for the radioopacity is thereby provided in the raw image. Using this measure, the raw image can be calibrated automatically, i.e., the structures of the body part shown in the raw image can be assessed in an objective manner with regard to their radioopacity. This facilitates the interpretation of the three-dimensional image. It is in particular possible to differentiate more easily and safely between bones and tissue, which is essential in dental implantology. The marker support may comprise a plurality of radioopacity spectra distributed across the body part or the image space, each of the spectra comprising a plurality of marker elements of different radioopacity, so that a local calibration can be performed. This allows addressing the fact that, due to principle-related reasons, the imaging quality in digital volume tomography can locally vary significantly.

In an embodiment of the present invention, the marker support can, for example, be designed as an intraoral marker support and a plurality of marker elements are arranged within the dental arch. For example, at least one marker element can be arranged outside the dental arch or, for example, outside a patient's mouth. A positioning outside the dental arch or a patient's mouth allows for the generation of calibration values, for example, in the region of the jaw bone of a patient's jaw. It is in this region that a high accuracy is desired for the planning of an implant.

The following is a detailed description of two embodiments of the present invention with reference to the drawings.

The embodiments illustrated in the Figures refer to a dental application, the body part being a patient's jaw in the present case.

Figure 2:
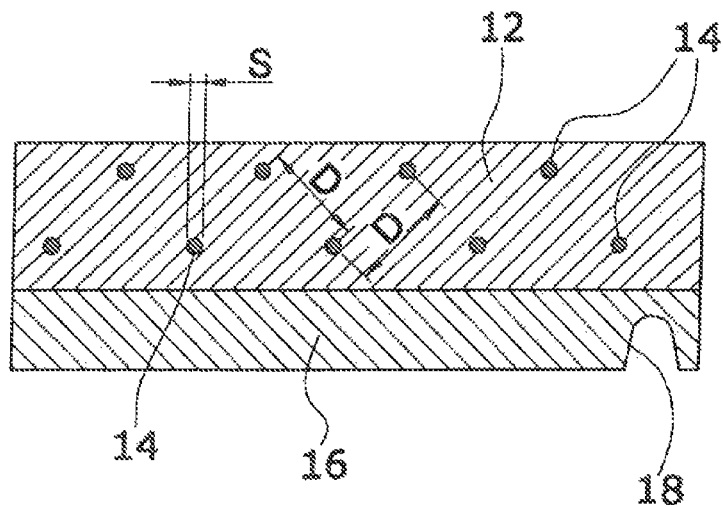
FIG. 2 shows a longitudinal section of the marker support in FIG. 1.

FIGS. 1 and 2 schematically illustrate an intraoral marker support 10 suitable for generating a radiologic three-dimensional image with a digital volume tomography apparatus. The marker support 10 is formed by a radiologically invisible support body 12 of a suitable plastic material. An individually shaped part 16 is attached, e.g., by gluing, to the support body 12, the shaped part having tooth recesses 18 that are shaped complementary to the patient's teeth. The individually shaped part 16, which is an impression of the relevant jaw 22, 23 of the patient, provides a firm, immovable and defined fit of the marker support 10 on the patient's jaw 22, 23 in the patient's mouth.

In the support body 12, radiologically visible, i.e., radioopaque, marker elements 14 are arranged in two planes and with a regular distribution. Three neighboring marker elements 14 respectively form an equilateral triangle and are spaced from each other by a nominal distance D that is equal for all marker elements 14 and is not larger than 3.0 cm. All marker elements 14 are of an identical size S which, for example, with spherical marker elements 14, corresponds to the diameter. The size S is a few millimeters at most.

Figure 3:
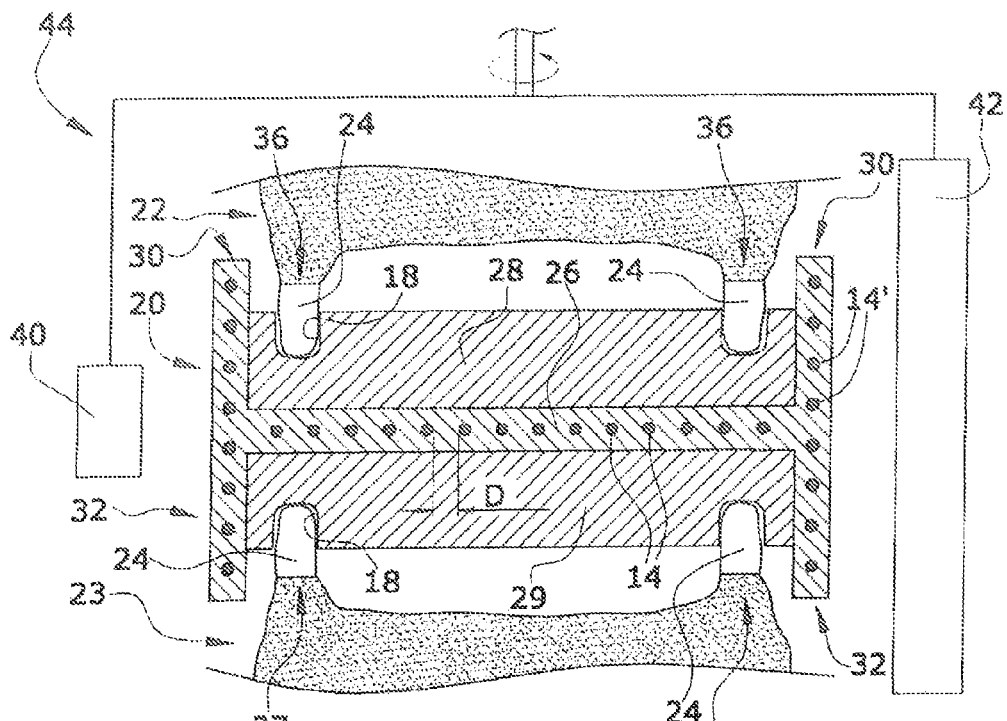
FIG. 3 shows a cross section of a patient's jaw with the intraoral marker support in place and a digital volume tomography apparatus.
Figure 4:
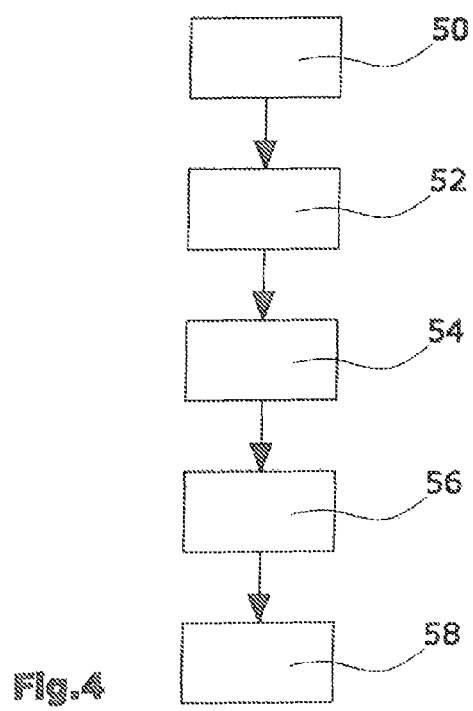
FIG. 4 shows a flow diagram of a method for generating a radiologic three-dimensional image of a patient's head.

FIG. 3 illustrates a second embodiment of a more complex marker carrier 20 set in the mouth of a patient. A rotor 44 of a digital volume tomography apparatus, rotating about a vertical axis, is shown which carries an X-ray radiation source 40 generating a cone-shaped X-ray beam and a two-dimensional detector 42 opposite the source.

The marker support 20 is H-shaped in cross section and has a horizontal support body 26 and vertical support body members 30, 32 projecting upward and downward from the outer circumference thereof. In the ground, planes of the support body members 26, 30, 32, the respective marker elements 14 are distributed in a two-dimensional manner. An individually shaped part 28, 29 is fixed respectively on the top and the bottom of the horizontal support body member, the individually shaped part 28, 29 being obtained by an impression of the upper jaw 22 or the lower jaw 23. The arrangement of the marker elements 14 generally corresponds to that in the marker support 10 of FIGS. 1 and 2.

Most marker elements 14 in the horizontal support body member 26 are arranged within the dental arches 36, 37 set up by the patient's teeth 24 in the patient's upper jaw 22 and lower jaw 23. The marker elements 14' in the vertical support body members 30, 32 are in particular arranged outside the dental arches 36, 37, but inside the patient's mouth.

The method for generating a radiological three-dimensional image of the patient's jaw is carried out as follows:

In a first method step 50, the marker support 20 is first set into the patient's mouth. The marker support 20 is fixed in the patient's mouth by the patient biting thereon.

Thereafter, in the next method step 52, the digital volume tomography apparatus is used to make a scan of the patient's jaw in order to generate a three-dimensional raw image of the patient's head or jaw, respectively. Subsequently, in a further method step 54, the size S' and the mutual distances D' of the marker elements in the raw image are measured for all the marker elements.

Thereafter, in the following method step 56, the measured values of the marker element distances D' are matched against the known nominal value D or a quotient is generated therefrom, respectively. From the local quotients of the raw image distances D' and the constant nominal distances D between the marker elements, a correction value QD is generated directly so as to locally correct the raw image in a subsequent method step 58. The correction is always a size correction based on the raw image distances D' in relation to the mutual nominal distances D of the marker elements.

The thus obtained three-dimensional corrected image of the patient's head or the patient's jaw is significantly more precise than the raw image, in particular with respect to proportions and distances. In this manner, an exact three-dimensional image of the patient's jaw is provided, in particular for the planning of dental implants, which image forms the basis of the subsequent accurate planning and realization of the implantologic dental treatment.

In addition to this, a plurality of local quality indicators QS are indicated or shown in the corrected raw image, whose value is obtained from the relative aberration of the raw image size S' from the nominal size S of the marker elements. The size quality indicator QS provides information about the quality degree of the raw image at the relevant location, and in particular provides information on the degree of reliability of the raw image or the corrected raw image.

The radioopacity of the marker elements 14, 14' differs. With respect to the embodiment of FIG. 3, the vertical support body member 30 may be provided at four positions of the dental arch with a range of three to six vertically spaced marker elements 14' of different radioopacity. These are used in the raw image to locally calibrate the raw image with respect to its brightness and its contrast. This calibration may well vary in the four regions. The image obtained significantly facilitates the differentiation between bones and tissue.

The present invention is not limited to embodiments described herein; reference should be had to the appended claims.

What is claimed is:

1. A method for generating a radiologic three-dimensional digital volume tomography image of a patient's jaw for use in planning a dental implant, the method comprising:
   fixing a marker support to the patient's jaw, wherein the marker support is provided with a non-radioopaque support body in which at least 10 spherical radioopaque marker elements are affixed as a grid, and wherein at least one of a nominal size S and a nominal distance D of the spherical radioopaque marker elements to each other is known;
   image recording the jaw with a digital volume tomography device so as to generate a three-dimensional raw image of the patient's jaw;
   measuring at least one of a size S' and a distance D' of the spherical radioopaque marker elements in the three-dimensional raw image;
   generating an aberration value by comparing at least one of the size S' and the distance D' of the spherical radioopaque marker elements in the three-dimensional raw image with the respective at least one of the nominal size S and the nominal distance D of the spherical radioopaque marker elements; and
   correcting the three-dimensional raw image with the aberration value so as to generate an exact radiologic three-dimensional digital volume tomography image of the patient's jaw;
   wherein, each spherical radioopaque marker element has a constant nominal distance D to each neighboring spherical radioopaque marker.

2. The method as recited in claim 1, wherein the marker support is fixed to a patient's mouth.

3. The method as recited in claim 1, wherein the correcting of the three-dimensional raw image with the aberration value is a size correction of the three-dimensional raw image with the distance D' in relation to the nominal distance D of the spherical radiopaque marker elements.

4. The method as recited in claim 3, wherein each spherical radioopaque marker element has a constant nominal distance D of a maximum of 3.0 cm to a neighboring spherical radioopaque marker element, wherein the aberration value is a local aberration value, and wherein more than one size correction is performed locally with the local aberration value.

5. The method as recited in claim 4, wherein three neighboring spherical radioopaque marker elements respectively form an equilateral triangle.

6. The method as recited in claim 1, further comprising providing a quality indicator value, whereby the quality indicator value is based on a difference of the size S' to the nominal size S of the spherical radioopaque marker elements.

7. The method as recited in claim 1, wherein the spherical radioopaque marker elements are arranged in at least two transversal planes.

8. The method as recited in claim 1, wherein a radioopacity of the spherical radioopaque marker elements is different, and further comprising:
   calibrating a brightness of the three-dimensional raw image based on known different radioopacity values of the spherical radioopaque marker elements.

9. The method as recited in claim 1, wherein the spherical radioopaque marker elements are provided inside a dental arch.

10. The method as recited in claim 9, wherein at least one spherical radioopaque marker element is provided outside of a patient's mouth.

11. The method as recited in claim 9, wherein at least one spherical radioopaque marker element is provided outside the dental arch.

12. The method as recited in claim 11, wherein at least one spherical radioopaque marker element is provided outside of a patient's mouth.

13. The method as recited in claim 1, wherein the spherical radioopaque marker elements are arranged in at least one of two planes and with an H-shaped cross-section.

14. The method as recited in claim 1, wherein the correcting the three-dimensional raw image with the aberration value performs at least one local size correction.

* * * * *